(12) United States Patent
Tan

(10) Patent No.: US 10,098,345 B2
(45) Date of Patent: Oct. 16, 2018

(54) WATER RESISTANT DISINFESTATION SHEET AND METHOD OF MANUFACTURING

(71) Applicant: Dong Lin Eugene Tan, Singapore (SG)

(72) Inventor: Dong Lin Eugene Tan, Singapore (SG)

(*) Notice: Subject to any disclaimer, the term of this patent is extended or adjusted under 35 U.S.C. 154(b) by 0 days.

(21) Appl. No.: 15/556,160

(22) PCT Filed: Aug. 10, 2016

(86) PCT No.: PCT/SG2016/050382
§ 371 (c)(1),
(2) Date: Sep. 6, 2017

(87) PCT Pub. No.: WO2017/146642
PCT Pub. Date: Aug. 31, 2017

(65) Prior Publication Data
US 2018/0049432 A1   Feb. 22, 2018

(30) Foreign Application Priority Data

Apr. 6, 2016  (CN) .......................... 2016 1 0208793

(51) Int. Cl.
*A01N 25/34* (2006.01)
*A01N 53/00* (2006.01)
*B29C 47/00* (2006.01)
*A01N 25/10* (2006.01)
*B32B 27/04* (2006.01)
*B32B 27/18* (2006.01)

(52) U.S. Cl.
CPC ............ *A01N 25/34* (2013.01); *A01N 25/10* (2013.01); *A01N 53/00* (2013.01); *B29C 47/0054* (2013.01); *B32B 27/04* (2013.01); *B32B 27/18* (2013.01); *B29C 47/0004* (2013.01)

(58) Field of Classification Search
CPC ........ A01N 25/34; A01N 25/10; A01N 53/00; B29C 47/0054; B32B 27/18
See application file for complete search history.

(56) References Cited

U.S. PATENT DOCUMENTS

| | | | |
|---|---|---|---|
| 2,434,709 A | 1/1948 | Matthews | |
| 5,641,499 A | 6/1997 | Bencsits | |
| 5,860,266 A | 1/1999 | Martinet et al. | |
| 2009/0314713 A1* | 12/2009 | Shelby | B01D 63/10 210/636 |
| 2012/0210630 A1 | 8/2012 | Ashley et al. | |

FOREIGN PATENT DOCUMENTS

| | | |
|---|---|---|
| CN | 101044847 A | 10/2007 |
| JP | 07-41402 A | 2/1995 |
| JP | H 10-17846 | 1/1998 |
| JP | 2000-54259 | 2/2000 |

* cited by examiner

*Primary Examiner* — Mina Haghighatian
(74) *Attorney, Agent, or Firm* — Baker & Hostetler LLP

(57) ABSTRACT

A disinfestation sheet includes a carrier layer with a first and second surface with active pesticidal particles formed therein. The active pesticidal particles contain pesticidal ingredients selected from pyrethroid family or the like. The carrier layer has channels formed therein. The channels form one or more paths between one or more pesticidal particles and at least one of the first and the second surfaces to allow diffusion of the active pesticidal ingredient from the pesticidal particles to at least one of the first and the second surfaces of the carrier layer. The disinfestation sheet may further comprise antioxidant compounds. The disinfestation sheet may also have a base layer attached to the second surface of the carrier layer, an adhesive grip layer attached to the base layer and a support layer attached to the grip layer, where in the support layer is detachable. The carrier layer may also comprise ridges extending outwardly from the second surface. A method of manufacturing a disinfestation sheet comprising the mixing and blow-extrusion of pesticidal and polymer pellets is also defined.

8 Claims, 8 Drawing Sheets

WATER RESISTANT DISINFESTATION SHEET AND METHOD OF MANUFACTURING

FIELD OF INVENTION

The present invention relates to pest control, in particular to a disinfestation sheet and a method of manufacturing a disinfestation sheet.

BACKGROUND OF INVENTION

Pests are ubiquitous in human lives. Bed bugs and dust mites are often unknowingly carried into bedrooms, hostels and dormitories, etc. Pest of such and other types cause itches, pain, allergies and respiratory syndromes. Flies, mosquitos, ants and cockroaches pollutes the environment, spreading bacteria and virus via kitchenware, utensils, food, etc., adversely affecting human health. Other pests infest food storages, collections and wooden products, causing irreparable losses. Traditional ways of exterminating the above mentioned pests are to apply insecticide sprays or pesticidal drugs.

Insecticide sprays have limited lasting longevity, hence requiring repeated application, adding in continuous pollution to the environment. Pesticides are highly toxic in large amounts and frequent applications, and would pose a threat in particular to children and pets if used under inadequate supervision.

Traditional methods are further limited by the area of application. For example, pesticides are difficult to be applied and retained on vertical or targeted surfaces or kept secured to a safe location. Hence it is desirable to have a solution in exterminating insects which is effective, convenient and safe.

SUMMARY OF INVENTION

Embodiments of the present invention provide a disinfestation sheet capable of being conveniently attached to a desired location for pest disinfestation. Embodiments of the invention also provides a method of manufacture of a disinfestation sheet.

In one embodiment, a disinfestation sheet includes a carrier layer with active pesticidal particles encapsulated therein. The active pesticidal particles contain pesticidal ingredients selected from pyrethroid family or the like. Pyrethroids may be produced and prepared from plant extracts. The carrier layer has channels formed therein. The channels form one or more paths between one or more pesticidal particles and at least one of the first and the second surfaces to allow diffusion of the active pesticidal ingredient from the pesticidal particles to at least one of the first and the second surfaces of the carrier layer. When pests move to become in contact with a disinfestation sheet, the pesticidal ingredient reacts with the pests' integral membrane protein, hindering the nerve cells and associated functions, eventually ceasing the functions of nerve cells and killing the pests within short period time.

The active pesticide ingredients may include active pyrethroid compounds, for example deltamethrin or cypermethrin. The carrier may be of a polymer medium such as polyethylene material. The carrier layer may include anti-ultraviolet compounds and antioxidant compounds.

The channels has cross sectional dimension suitable to allow contents of the active pesticidal ingredient diffused from the pesticidal particles to pass through and arrive at the top/bottom surface of the carrier layer, and to prevent liquid contents such as water from entering into the channels and contacting the pesticidal particles. As such, the disinfestation sheet is water resistant and can be used in both indoor and outdoor environments.

According to another embodiment, a disinfestation sheet may further comprise a base layer attached to the second surface of the carrier layer, a grip layer attached to the base layer and a support layer attached to the grip layer. The grip layer has an adhesive surface covered by the support layer, and the support layer is detachable from the grip layer to expose the adhesive surface.

In yet another embodiment, carrier layer comprises ridges extending outwardly from the second surface of the carrier layer. In a further embodiment, the carrier layer comprises projections extending outwardly from the second surface of the carrier layer.

In a method of manufacturing a disinfestation sheet, pesticidal material pellets and polymer material pellets are prepared and mixed together to form mixture. The mixture is processed in a thermal extrusion machine for blow-extruding to form a carrier layer in which, pesticidal material pellets are reformed into pesticidal particles and evenly distributed in the carrier layer. Channels are also formed in the carrier layer, forming paths between the pesticidal particles and the top and/or bottom surfaces of the carrier layer. An anti-ultraviolent compound, antioxidant compound, rheology modifiers, lubricant and LLDPE may be prepared and mixed with the pesticidal material pellets and the polymer material pellets.

When pests to become in contact with the disinfestation sheet, the pesticidal ingredients diffused from the carrier layer reacts with the pests' integral membrane protein, hindering the nerve cells and associated functions, eventually ceasing the functions of nerve cells and killing the pests within short period of time.

The disinfestation sheet can be integrated or applied on walls, pillars, dining furniture, mats, mattresses, pet beddings and the like. The resulting products are safe and while providing effective prevention and extermination of pests.

Other aspects and advantages of the present invention will become apparent from the following detailed description, illustrating by way of example the inventive concept and technical solution of the present invention.

BRIEF DESCRIPTION OF THE DRAWINGS

Embodiments of the invention are disclosed hereinafter with reference to the drawings, in which.

DETAILED DESCRIPTION OF THE PREFERRED EMBODIMENTS

Figure 1:
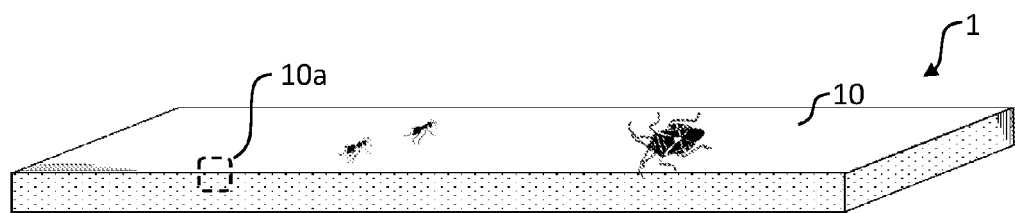
FIG. 1 is an isometric view of a disinfestation sheet according to a first embodiment of the present invention when used for pest disinfestation.
Figure 2:
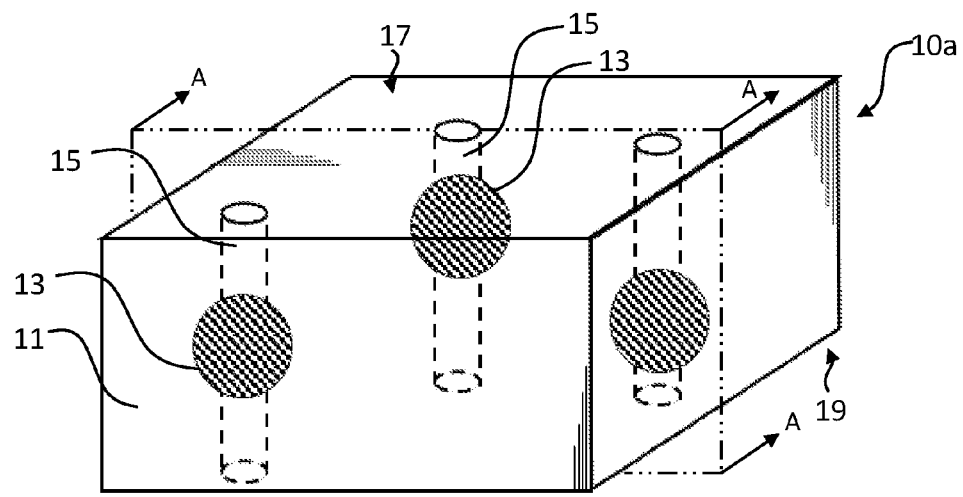
FIG. 2 is an enlarged partial view of FIG. 1.
Figure 3:
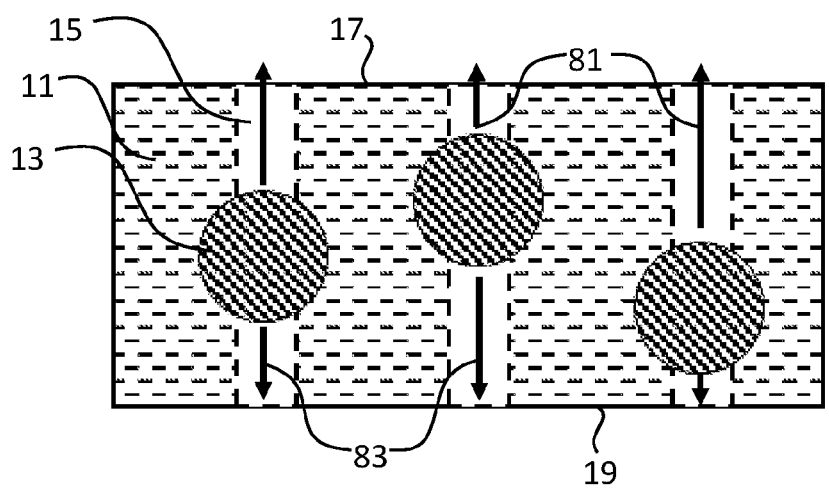
FIG. 3 is a cross sectional view of FIG. 2 along A-A.
Figure 4:
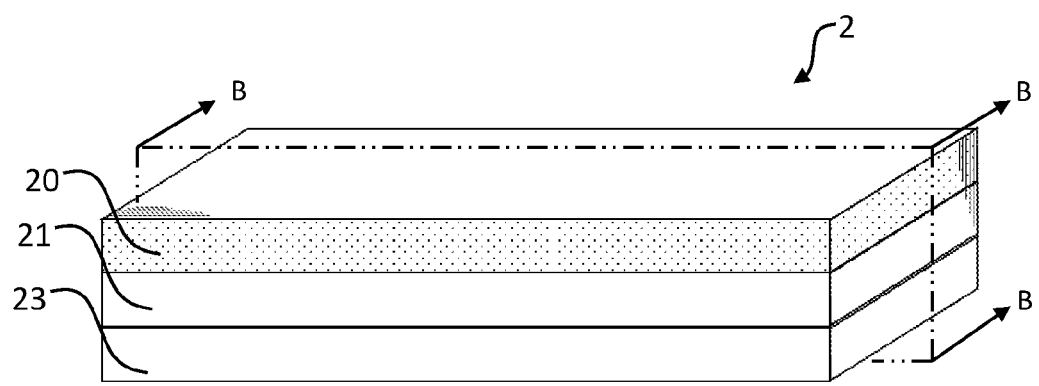
FIG. 4 is an isometric view of a second embodiment of the disinfestation sheet according to the present invention.

As shown in FIGS. 1 to 3, a disinfestation sheet 1 according to a first embodiment of the present invention includes a carrier layer 10, pesticidal particles 13 distributed in carrier 10, and channels 15 formed in carrier layer 10. Carrier layer 10 may be made of a polymer material 11 such as polyethylene, with pesticidal particles 13 distributed inside carrier layer 10. Carrier layer 10 is generally sheet-shaped having a first surface, e.g. top surface 17 and a second surface, e.g. bottom surface 19. Channel 15 form a path to connect one or more pesticidal particles 13 to the top surface 17 and/or bottom surface 19.

Pesticidal particles 13 may contain pesticidal ingredients of pyrethroid family, such as cypermethrin, deltamethrin, etc. Channels 15 allow diffusion of pesticidal ingredients from pesticidal particles 13 to the top surface 17 and/or bottom surface 19 of carrier layer 10. Accordingly, the pesticidal ingredients are continuously released from the pesticidal particles 13, travel through channels 15 along directions 81, 83 to become present at the top surface 17 and bottom surface 19 of carrier layer 10. When pests are in contact with disinfestation sheet 1 e.g. crawl onto the top surface 17, the pesticidal ingredients on and near the top surface and/or bottom surface 19 of carrier layer 10 react with the pests' integral membrane protein, hindering the pests' nerve cells and associated functions, eventually kill the pests within short period of time.

Additionally, pesticidal ingredients do not adhere to mammalian skin easily. In the event of being inhaled by a mammal or ingested into a mammal body, the pesticidal ingredients will be rapidly metabolized and degraded into non-toxic byproducts and metabolites to be eventually excreted. Thus pesticidal ingredients are innocuous and non-toxic to human body, rendering the disinfestation sheet safe for use.

The channels has cross sectional dimension suitable to allow contents of the active pesticidal ingredient diffused from the pesticidal particles to pass through and arrive at the top/bottom surface of the carrier layer, and to prevent liquid contents such as water from entering into the channels and contacting the pesticidal particles. As such, the disinfestation sheet is water resistant and can be used in both indoor and outdoor environments.

Carrier layer 10 may include anti-ultraviolet compounds and antioxidant compounds to hinder degradation of the carrier layer due to the possible effect of oxidation and/or ultraviolet irradiation from surrounding environment.

Figure 5:
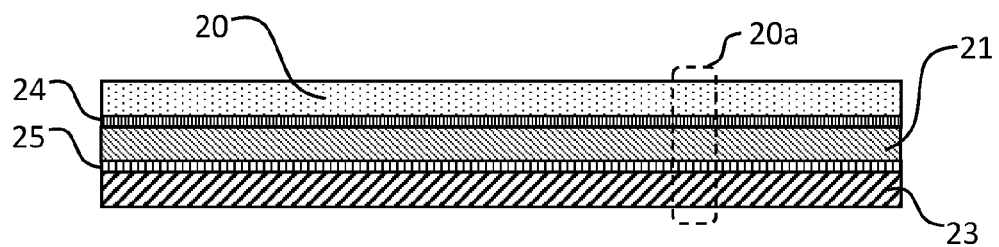
FIG. 5 is a cross sectional view of FIG. 4 along B-B.
Figure 6:
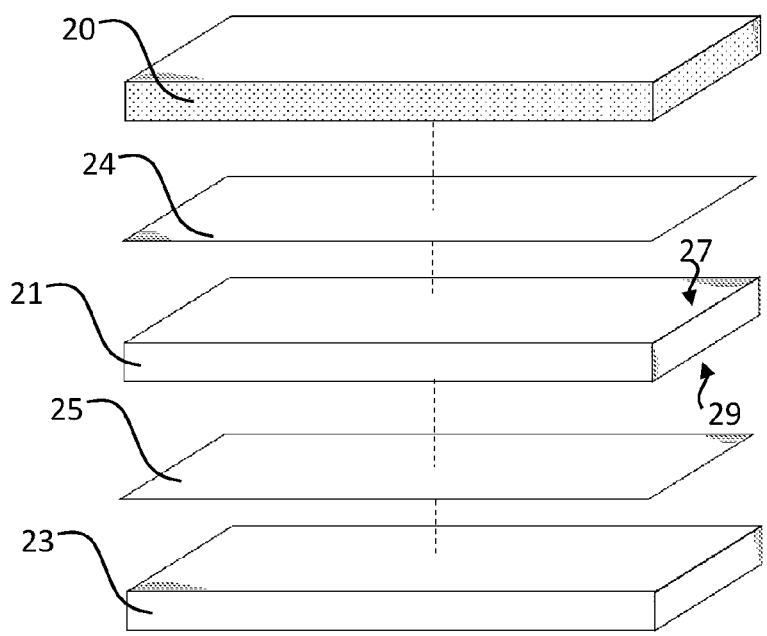
FIG. 6 is an exploded perspective view of FIG. 5.
Figure 7:
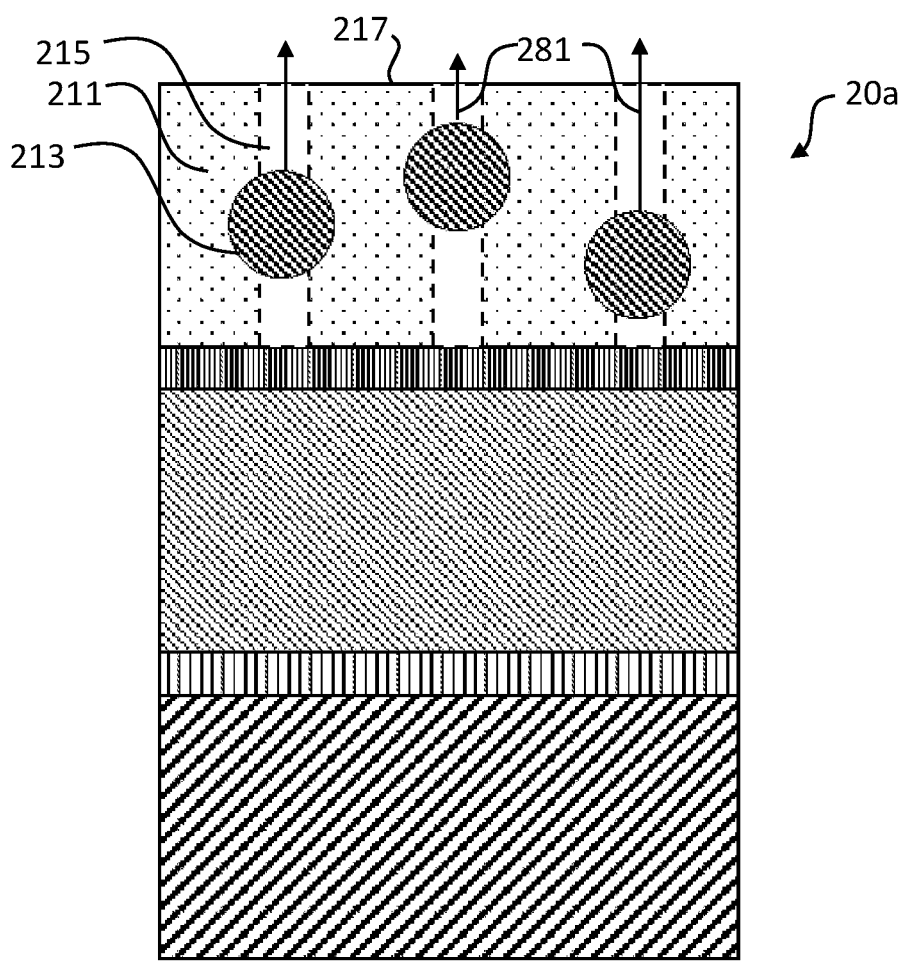
FIG. 7 is an enlarged partial view of FIG. 5.
Figure 8:
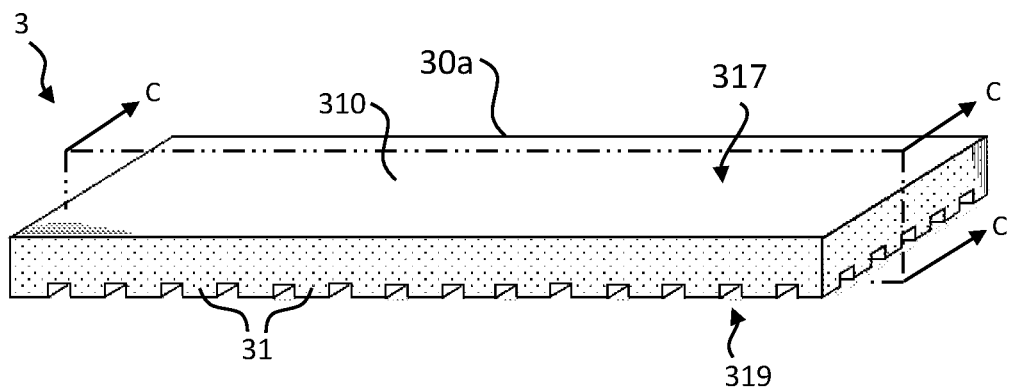
FIG. 8 is a perspective view of a third embodiment of the disinfestation sheet according to the present invention.
Figure 9:
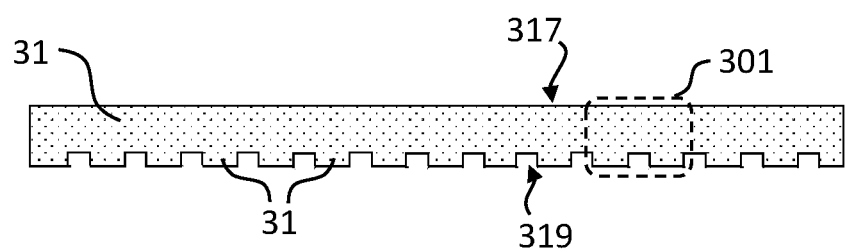
FIG. 9 is a cross sectional view of FIG. 8 along C-C.

According to a second embodiment, as shown in FIGS. 5 to 7, a disinfestation sheet 2 includes a carrier layer 20, pesticidal particles 213 distributed in carrier 20, and channels 215 formed in carrier 20. Carrier layer 20 may be made of a polymer material 211 such as polyethylene, with pesticidal particles 213 distributed inside carrier layer 20. Channel 215 form a path to connect one or more pesticidal particles 213 to top surface 217 of carrier layer 210. Pesticidal particles 213 may contain pesticidal ingredients of pyrethroid family, such as cypermethrin, deltamethrin, etc.

Channels 215 allows diffusion of pesticidal ingredients from pesticidal particles 213 to top surface 217 of carrier layer 210. Accordingly, the pesticidal ingredients are continuously released from the pesticidal particles, travel through channels 215 along direction 281 to become present at top surface 217 of carrier layer 20. When pests are in contact with disinfestation sheet 2 e.g. crawl onto the top surface 217, the pesticidal ingredients react with the pests' integral membrane protein, hindering the pests' nerve cells and associated functions, eventually kill the pests within short period of time.

Disinfestation sheet 2 includes a base layer 21 attached to carrier layer 20 and a support layer 23 attached to base layer 21. An adhesive layer 24 is disposed between carrier layer 20 and base layer 21, and a grip layer 25 is disposed between base layer 21 and support layer 23. Adhesive layer 24 serves to adhere carrier layer 20 to base layer 21. Grip layer 25 has adhesive on the surface to which support layer 23 is attached.

Base layer 21 is relatively more rigid than carrier layer 20, and may be made from material such as biaxially oriented polypropylene (BOPP). Base layer 21 is adhered to carrier layer 20 by adhesive layer 24. Base layer 21 is to hold the shape of the disinfestation sheet 2 to prevent disinfestation sheet 2 from collapsed or deformed.

Support layer 23 is used in providing a release effect against a sticky material such as an adhesive on the surface of grip layer 25. Support layer 23 protects grip layer 25 during shipment and storage of disinfestation sheet 2, to prevent a stack of disinfestation sheets from being adhered to each other. In use, support layer 23 is peeled off from grip layer 25 to expose the adhesive surface of grip layer 25, such that the disinfestation sheet 2 can be conveniently adhered at desirable location, such as on a wall. Attachment of disinfestation sheet 2 to a desired location by grip layer 25 allows the disinfestation sheet to be secured at locations without the need of using additional securement hardware such as hooks, tapes, or fasteners.

Referring to FIGS. 8 to 11, in a third embodiment, a disinfestation sheet 3 comprises a carrier layer 310, pesticidal particles 313 distributed in carrier 310, and channels 315 formed in carrier 310. Carrier layer 310 is generally sheet-shaped having a top surface 317 and a bottom surface 319. Channel 315 forms a path to connect one or more pesticidal particles 313 to the top surface 317 and/or bottom surface 319.

Pesticidal particles 313 may contain pesticidal ingredients of pyrethroid family, such as cypermethrin, deltamethrin, etc. Channels 315 allow diffusion of pesticidal ingredients from pesticidal particles 313 to the top surface 317 and/or bottom surface 319 of carrier layer 310. Accordingly, the pesticidal ingredients are continuously released from the pesticidal particles, travel through channels 315 along direction 381, 383 to become present at the top surface 317 and bottom surface 319 of carrier layer 310. When pests are in contact with disinfestation sheet 3 e.g. crawl onto the top surface 317, the pesticidal ingredients react with the pests' integral membrane protein, hindering the pests' nerve cells and associated functions, eventually kill the pests within short period of time.

Figure 10A:
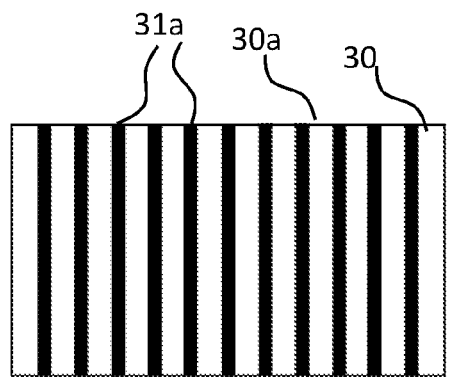
FIGS. 10A, 10B, 10C and 10D are plan views of various alternative structures of the disinfestation sheet shown in FIG. 8.
Figure 10B:
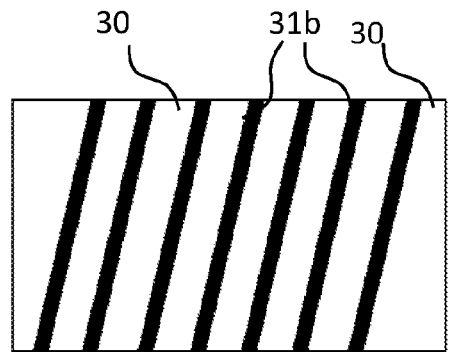
Figure 10C:
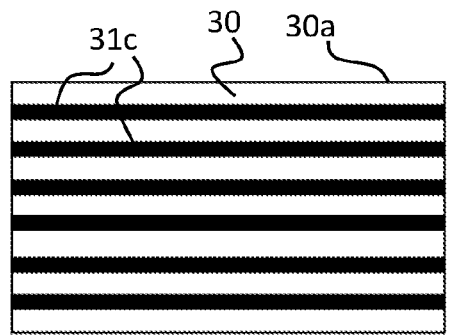
Figure 10D:
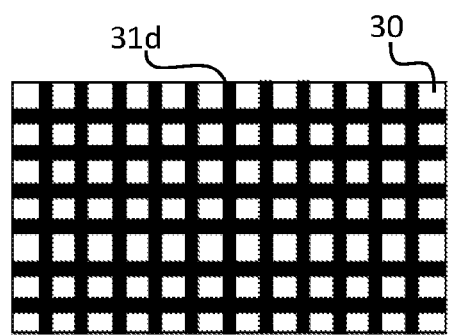
Figure 11:
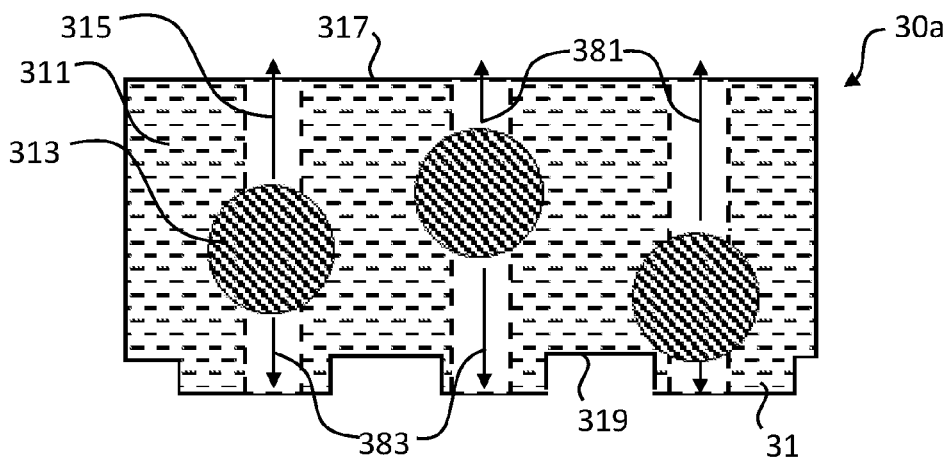
FIG. 11 is an enlarged cross sectional partial view of FIG. 8.

Bottom surface 319 includes projections 31 formed thereon. Projections 31 may be in in the form of a plurality of ridges 31a oriented perpendicular to an longitudinal side edge 30a of carrier layer 30 (FIG. 10A), ridges 31b oriented inclined, i.e. with an angle between 0 and 90 degrees, with respect to longitudinal side edge 30a of carrier 30a (FIG. 10B), ridges 31c parallel to longitudinal side edge 30a of carrier layer 310 (FIG. 10C), or a combination of perpendicular-oriented and parallel-oriented ridges forming a crossed ridge network 30d (FIG. 10D). In use, disinfestation sheet 3 is laid or attached with bottom surface 319 contacting a surface e.g. a table top. Ridges 31 increase the gripping effect between the disinfestation sheet 3 and the surface of placement, holding disinfestation sheet 3 in a desired position.

Figure 12:
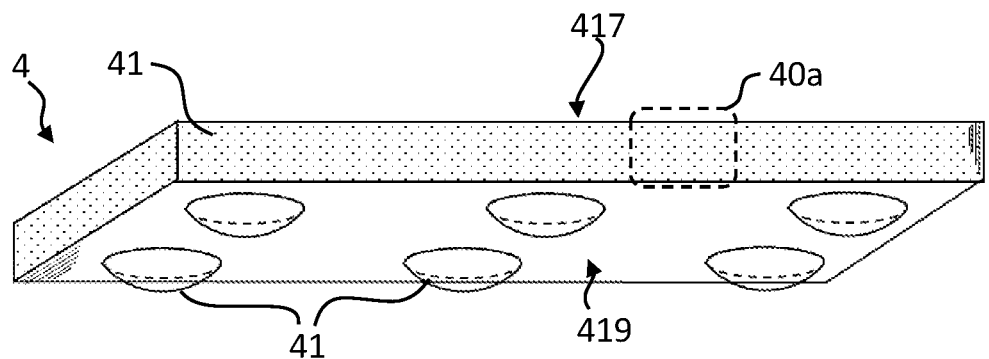
FIG. 12 is a perspective view of a fourth embodiment of the disinfestation sheet according to the present invention.
Figure 13:
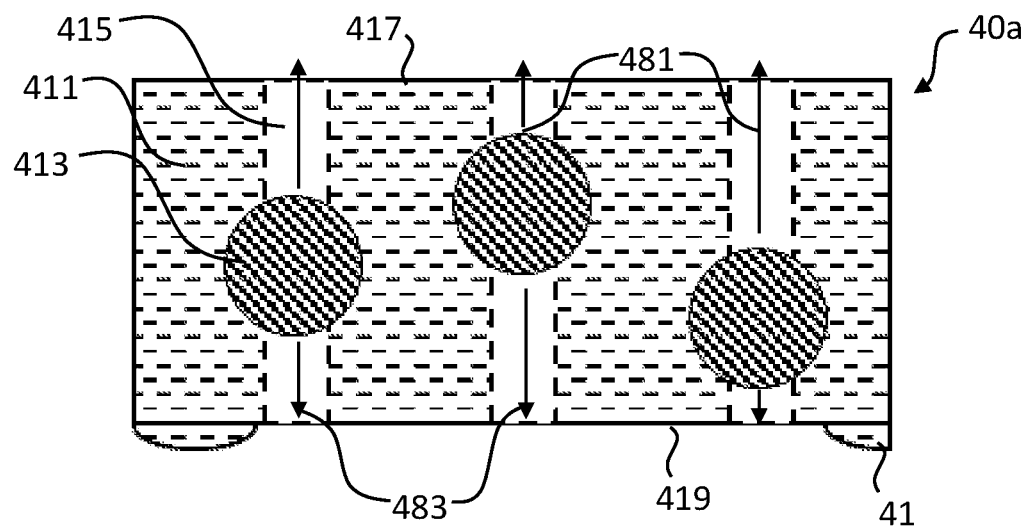
FIG. 13 is an enlarged cross sectional partial view of FIG. 12.

Referring to FIGS. 12 and 13, in a fourth embodiment, a disinfestation sheet 4 comprises a carrier layer 410, pesticidal particles 413 distributed in carrier 410, and channels 415 formed in carrier 410. Carrier layer 410 is generally sheet-shaped having a top surface 417 and a bottom surface 419. Channel 415 form a path to connect one or more pesticidal particles 413 to the top surface 417 and/or bottom surface 419.

Pesticidal particles 413 may contain pesticidal ingredients of pyrethroid family, such as cypermethrin, deltamethrin, etc. Channels 415 allow diffusion of pesticidal ingredients from pesticidal particles 413 to the top surface 417 and/or bottom surface 419 of carrier layer 410. Accordingly, the pesticidal ingredients are continuously released from the pesticidal particles, travel through channels 415 along direction 481, 483 to become present at the top surface 417 and bottom surface 419 of carrier layer 410. When pests are in contact with disinfestation sheet 4 e.g. crawl onto the top surface 417, the pesticidal ingredients react with the pests' integral membrane protein, hindering the pests' nerve cells and associated functions, eventually kill the pests within short period of time.

Bottom surface 419 includes projections 41 formed thereon. Projections 41 may be in in form of bumps bossed from bottom surface 419. In use, disinfestation sheet 4 is laid or attached with bottom surface 419 contacting a surface e.g. a table top. Projections 41 increase the friction between the disinfestation sheet 3 and the surface of placement, holding disinfestation sheet 3 in a desired position.

Figure 14:
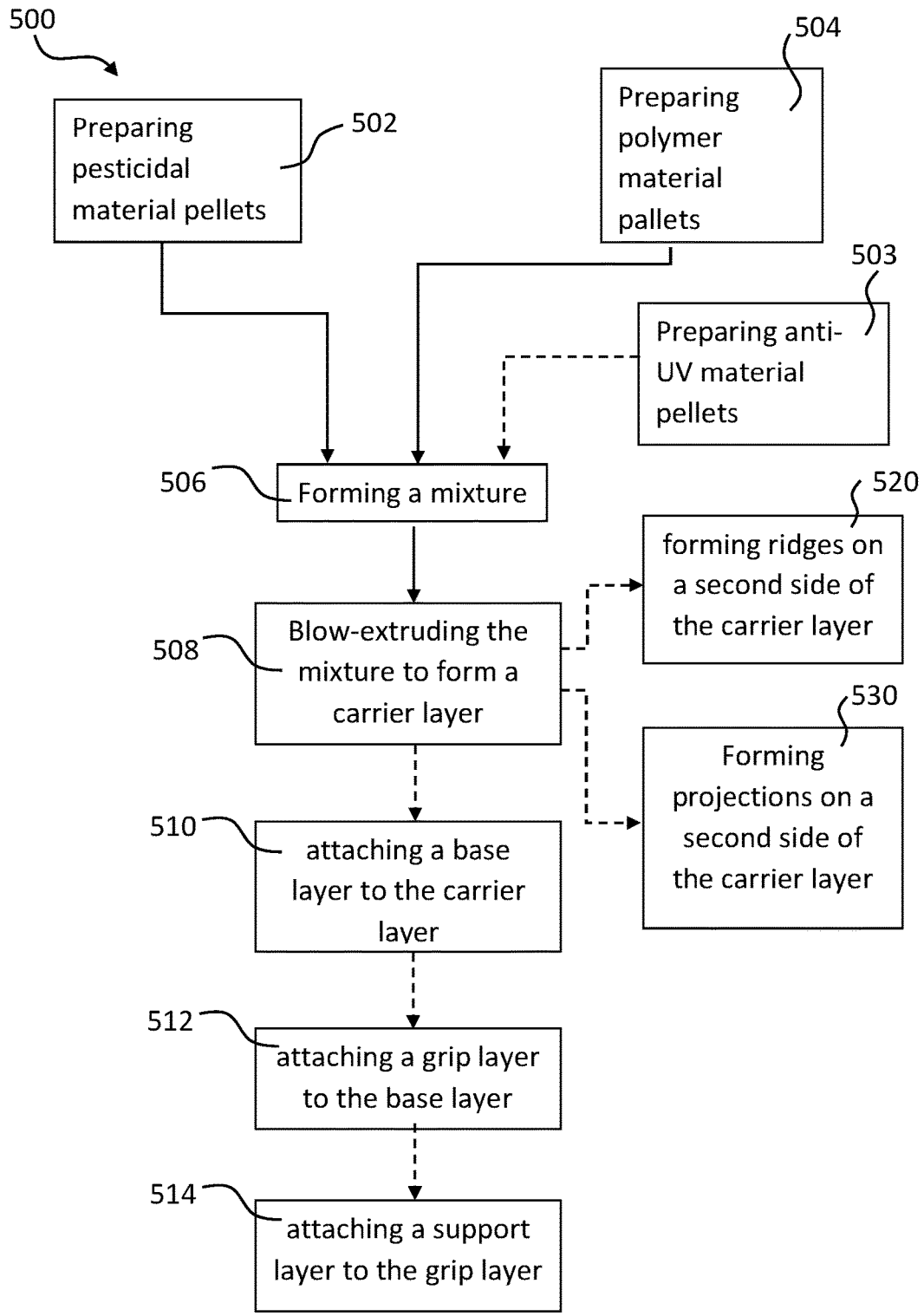
FIG. 14 is a flowchart of a method for manufacturing a disinfestation sheet according to an embodiment of the present invention.

As shown in FIG. 14, in a method 500 of manufacturing a disinfestation sheet according to the embodiments illustrated above, at steps 502 and 504, pesticidal material pellets and polymer material pellets e.g. linear low-density polyethylene (LLDPE), are prepared. At step 506, the pesticidal material pellets and polymer material pellets are mixed to form a mixture. At step 508, the mixture is blow-extruded in a thermal extrusion machine to form a carrier layer. During the blow-extrusion process, the pesticidal material pellets and polymer material pellets are molten and evenly mixed together, resulting in even distribution of pesticidal particles in the carrier layer, and channels formed in the carrier payer. Optionally, anti-UV material pellets may be prepared at step 503, and mixed with the pesticidal material pellets and polymer material pellets and loaded into the thermal extrusion machine for blow extrusion. The carrier layer produced may have a thickness ranging from 0.05 mm to 0.8 mm depending.

To form a disinfestation sheet according to the second embodiment illustrated above, a base layer is attached to the carrier layer at step 510, and a grip layer is attached to the base layer at step 512. Hereafter, at step 514, a support layer is attached to the grip layer.

To form a disinfestation sheet according to the third embodiment illustrated above, the carrier layer formed at step 508 is further processed at step 520 to form ridges on a second side of the carrier. To form a disinfestation sheet according to the fourth embodiment illustrated above, the carrier layer formed at step 508 is further processed at step 530 to form projections on a second side of the carrier.

It should be appreciated that the present invention is not to be limited in scope by the specific embodiments described here in. Various modifications of the invention in addition to those described herein will become apparent to those skilled in the art from the foregoing description and accompanying drawings. Such modifications are intended to fall within the scope of the claims appended therein.

The invention claimed is:

1. A disinfestation sheet, comprising:
   a carrier layer having a first surface and a second surface, pesticidal particles disposed in the carrier layer, and channels formed in the carrier layer;
   a base layer attached to the second surface of the carrier layer, wherein the base layer is relatively more rigid than the carrier layer;
   a grip layer attached to the base layer; and
   a support layer attached to the grip layer,
   wherein the grip layer has an adhesive surface covered by the support layer, and
   wherein the support layer is detachable from the grip layer to expose the adhesive surface,
   wherein the pesticidal particles contain an active pesticidal ingredient, and
   wherein one or more of the channels form one or more paths between one or more pesticidal particles and at least one of the first and the second surfaces to allow diffusion of the active pesticidal ingredient from the pesticidal particles to at least one of the first and the second surfaces of the carrier layer.

2. The disinfestation sheet as recited in claim 1, wherein the carrier layer comprises anti ultraviolet compounds and anti-oxidant compounds.

3. The disinfestation sheet as recited in claim 1, wherein the carrier layer further comprises ridges extending outwardly from the second surface.

4. The disinfestation sheet as recited in claim 3, wherein the ridges are oriented perpendicular to a longitudinal side edge of the carrier layer.

5. The disinfestation sheet as recited in claim 3, wherein the ridges are oriented parallel to a longitudinal side edge of the carrier layer.

6. The disinfestation sheet as recited in claim 3, wherein the ridges are oriented inclined with respect to a longitudinal side edge of the carrier layer.

7. The disinfestation sheet as recited in claim 3, wherein the ridges includes a combination of perpendicular-oriented and parallel-oriented ridges forming a crossed ridge network.

8. The disinfestation sheet as recited in claim 3, wherein the ridges provide for gripping between the disinfestation sheet and a surface of placement, thereby holding disinfestation sheet in a position.

* * * * *